United States Patent
Tseng et al.

(10) Patent No.: US 10,959,646 B2
(45) Date of Patent: Mar. 30, 2021

(54) IMAGE DETECTION METHOD AND IMAGE DETECTION DEVICE FOR DETERMINING POSITION OF USER

(71) Applicant: Yun yun AI Baby camera Co., Ltd., Taipei (TW)

(72) Inventors: Chih-Hsin Tseng, Taipei (TW); Hsueh-Far Hsu, Taipei (TW); Kang-Ning Shan, Taipei (TW); Hsin-Yi Lin, Taipei (TW); Bo-Zong Wu, Taipei (TW); Shih-Yun Shen, Taipei (TW)

(73) Assignee: YUN YUN AI BABY CAMERA CO., LTD., Taipei (TW)

( * ) Notice: Subject to any disclaimer, the term of this patent is extended or adjusted under 35 U.S.C. 154(b) by 0 days.

(21) Appl. No.: 16/557,462

(22) Filed: Aug. 30, 2019

(65) Prior Publication Data
US 2020/0069222 A1    Mar. 5, 2020

(30) Foreign Application Priority Data
Aug. 31, 2018 (TW) .................. 107130639

(51) Int. Cl.
| | | |
|---|---|---|
| *G08B 23/00* | (2006.01) | |
| *A61B 5/11* | (2006.01) | |
| *G08B 21/04* | (2006.01) | |
| *A61B 5/00* | (2006.01) | |

(52) U.S. Cl.
CPC .......... *A61B 5/1116* (2013.01); *A61B 5/4806* (2013.01); *G08B 21/0476* (2013.01); *A61B 2503/04* (2013.01); *A61B 2503/06* (2013.01); *A61B 2503/08* (2013.01)

(58) Field of Classification Search
CPC . A61B 5/1116; A61B 5/4806; A61B 2503/04; A61B 2503/06; A61B 2503/08; G08B 21/0476
USPC ........................................... 340/575
See application file for complete search history.

(56) References Cited

U.S. PATENT DOCUMENTS

| | | | |
|---|---|---|---|
| 5,802,494 A | 9/1998 | Kuno | |
| 10,447,972 B2* | 10/2019 | Patil | ................. G06K 9/00389 |
| 10,699,107 B2* | 6/2020 | Chen | ................. G06K 9/00369 |
| 2008/0172795 A1 | 7/2008 | Straub | |

(Continued)

FOREIGN PATENT DOCUMENTS

| | | |
|---|---|---|
| CN | 204190864 U | 3/2015 |
| TW | I263944 B | 10/2006 |

(Continued)

OTHER PUBLICATIONS

TW Office Action dated Sep. 20, 2019, Application No. TW107130637, pp. 1-11.

*Primary Examiner* — Zhen Y Wu
(74) *Attorney, Agent, or Firm* — McClure, Qualey & Rodack, LLP

(57) ABSTRACT

An image detection method for determining positions of a user. According to the image detection method, a plurality of images of the user are obtained, whether the user moves is determined according to the images, a plurality of feature parameters of the plurality of images are obtained, and a body distribution analysis and a face occlusion analysis are performed to determine the position of the user.

12 Claims, 16 Drawing Sheets

(56) References Cited

U.S. PATENT DOCUMENTS

| | | | |
|---|---|---|---|
| 2010/0054549 A1* | 3/2010 | Steinberg | H04N 5/2354 382/118 |
| 2010/0183218 A1* | 7/2010 | Naito | G06K 9/00281 382/159 |
| 2011/0316705 A1 | 12/2011 | deVries et al. | |
| 2012/0026308 A1* | 2/2012 | Johnson | G06T 7/73 348/77 |
| 2014/0067679 A1* | 3/2014 | O'Reilly | G06Q 20/40145 705/44 |
| 2014/0232739 A1* | 8/2014 | Kim | G09G 5/14 345/592 |
| 2015/0141762 A1 | 5/2015 | Heinrich et al. | |
| 2015/0279113 A1* | 10/2015 | Knorr | G06T 15/50 345/633 |
| 2016/0110586 A1* | 4/2016 | Hayasaka | G06K 9/00281 382/118 |
| 2016/0171293 A1* | 6/2016 | Li | G06T 7/90 382/103 |
| 2016/0192876 A1 | 7/2016 | Proud | |
| 2016/0203305 A1* | 7/2016 | Suh | G06F 21/32 382/118 |
| 2017/0169113 A1* | 6/2017 | Bhatnagar | G06F 16/9535 |
| 2017/0319376 A1 | 11/2017 | Lo et al. | |
| 2018/0035082 A1* | 2/2018 | Patil | G06T 7/246 |
| 2018/0173980 A1* | 6/2018 | Fan | G06K 9/2027 |
| 2018/0285628 A1* | 10/2018 | Son | G06K 9/00228 |
| 2018/0285630 A1* | 10/2018 | Han | G06K 9/2054 |
| 2018/0373924 A1* | 12/2018 | Yoo | G06F 21/32 |
| 2019/0122039 A1* | 4/2019 | Chen | G06K 9/6255 |
| 2019/0205616 A1* | 7/2019 | Hong | G06K 9/00228 |
| 2019/0384969 A1* | 12/2019 | Shimauchi | G06K 9/4642 |
| 2019/0392564 A1* | 12/2019 | Sun | G06T 5/009 |
| 2020/0069222 A1* | 3/2020 | Tseng | A61B 5/4806 |
| 2020/0082157 A1* | 3/2020 | Susskind | G06K 9/00597 |

FOREIGN PATENT DOCUMENTS

| | | |
|---|---|---|
| TW | I415032 B | 11/2013 |
| TW | M480134 U | 6/2014 |
| TW | M529907 U | 10/2016 |
| TW | M537277 U | 2/2017 |
| TW | 201739416 A | 11/2017 |
| TW | M566889 U | 9/2018 |

* cited by examiner

IMAGE DETECTION METHOD AND IMAGE DETECTION DEVICE FOR DETERMINING POSITION OF USER

CROSS REFERENCE TO RELATED APPLICATIONS

This Application claims priority of Taiwan Patent Application No. 107130639, filed on Aug. 31, 2018, the entirety of which is/are incorporated by reference herein.

BACKGROUND OF THE INVENTION

Field of the Invention

The invention relates to an image detection method and an image detection device, and more particularly to an image detection method and an image detection device for determining positions of users.

Description of the Related Art

Many detection techniques can be applied to determine physiological parameters and body position of a user for the purpose of monitoring and caring for a baby, a child, a patient, or an elderly person. Although the sleeping position of a user can be determined by detecting facial features, facial features are rather unstable. There are more features in the frontal face. Thus, the detection rate is higher, and the detection rate of the lateral face is much lower.

Although the physiological information of the user can be obtained by wearing a smart wearable device, such as a wristband, there may be the problem of insufficient power. In addition, wearing a smart wearable device may be inconvenient or make the user feel uncomfortable. Therefore, there is a need for an image detection method and an image detection device capable of improving recognition and detection efficiency.

BRIEF SUMMARY OF THE INVENTION

In order to solve the above problems, the present invention provides an image detection method and an image detection device for determining a position of a user. In the present invention, a plurality of feature parameters of the images of the user are obtained, and a body distribution analysis and a face occlusion analysis are performed to determine the position of the user. The image detection method provided by the present invention adopts an artificial intelligence neural network architecture, and performs a dual analysis of the body distribution and the face occlusion, so as to accurately determine the position of the user, thereby achieving the purpose of care.

One embodiment of the present invention provides an image detection method for determining the position of a user. The image detection method comprises the steps of obtaining a plurality of images of the user; determining whether the user moves according to the images; obtaining a plurality of feature parameters of the plurality of image; and performing a body distribution analysis and a face occlusion analysis on the plurality of images according to the feature parameters to determine the position of the user.

In detail, the image detection method of the present invention further comprises the steps of dividing each of the plurality of images of the user into a plurality of region bases; calculating detection results of the plurality of feature parameters in each of the plurality of region bases; and determining the position of the user according to the detection results. The image detection method of the present invention also comprises the following step: in response to determining that the position of the user is sleeping on his side or in the prone position and a determined confidence level being lower than a predetermined confidence level, determining or modifying the position of the user according to the result of a face occlusion analysis.

Another embodiment of the present invention provides an image detection method for determining the position of a user. The image detection method comprises the steps of obtaining a plurality of images of the user; marking a plurality of feature parameters in the plurality of images; evaluating detection results of the plurality of feature parameters in each of the plurality of images; performing a body distribution analysis on the plurality of images according to the detection result of at least one first feature parameter among the plurality of feature parameters to determine first position information of the user; and performing a face occlusion analysis on the plurality of images according to the detection result of at least one second feature parameter among the plurality of feature parameters and the first position information to determine second position information of the user. The at least one second feature parameter is different from the at least one first feature parameter, and the second position information represents the posture of the user.

Another embodiment of the present invention provides an image detection method for determining the position of a user. The image detection method comprises the steps of obtaining a plurality of images of the user; obtaining a plurality of feature parameters of the plurality of images; performing a face occlusion analysis on the plurality of images according to the plurality of feature parameters to determine whether the plurality of images clearly show the user's face; determining a plurality of feature vectors and performing a body distribution analysis on the plurality of images according to the plurality of feature vectors to determine a body position and a position type of the user; and selecting an image regarding the position type according to results of the face occlusion analysis and the body distribution analysis.

Another embodiment of the present invention provides an image detection device for determining the position of a user. The image detection device comprises a sensor, a notification device, and a processor. The sensor captures a plurality of images of the user. The processor determines whether the user moves according to the plurality of images and obtains a plurality of feature parameters of the plurality of images. The processor performs a body distribution analysis and a face occlusion analysis on the images according to the feature parameters to determine the position of the user.

Another embodiment of the present invention provides an image detection device for determining the position of a user. The image detection device comprises a sensor and a processor. The processor comprises a body distribution analysis module and a face occlusion analysis. The sensor capturing a plurality of images of the user. The data marking module marks a plurality of feature parameters in the plurality of images. The feature analysis module calculates detection results of the plurality of feature parameters in each of the plurality of images. The body distribution analysis module performs a body distribution analysis on the plurality of images according to the detection result of at least one first feature parameter among the plurality of feature parameters to determine first position information of the user. The face occlusion analysis module performs a face occlusion analysis on the plurality of images according to the detection result of at least one second feature parameter among the plurality of feature parameters and the first position information to determine second position information of the user. The at least one second feature parameter is different from the at least one first feature parameter, and the second position information represents the position of the user.

Another embodiment of the present invention provides an image detection device for determining the position of a user. The image detection device comprises a sensor and a processor. The sensor captures a plurality of images of the user. The processor comprises a data marking module, a body distribution analysis module, and a face occlusion analysis module. The data marking module obtains a plurality of feature parameters of the plurality of images. The face occlusion analysis module performs a face occlusion analysis on the plurality of images according to the plurality of feature parameters to determine whether the plurality of images clearly show the user's face. The body distribution analysis module determines a plurality of feature vectors and performs a body distribution analysis on the plurality of images according to the plurality of feature vectors to determine a body position and a position type of the user. The processor selects an image related to the position type according to results of the face occlusion analysis and the body distribution analysis.

With regard to other additional features and advantages of the present invention, those skilled in the art can use the image detection method and the image detection device disclosed in the method of the present invention without departing from the spirit and scope of the present invention.

A detailed description is given in the following embodiments with reference to the accompanying drawings.

BRIEF DESCRIPTION OF THE DRAWINGS

The full disclosure is based on the following detailed description and in conjunction with the drawings. It should be noted that the illustrations are not necessarily drawn to scale in accordance with the general operation of the industry. In fact, it is possible to arbitrarily enlarge or reduce the sizes of the components for a clear explanation.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The following description provides many different embodiments or examples to implement various features of the present invention. The following description sets forth specific examples of various components and their arrangement to simplify the description. Of course, these specific examples are not intended to limit the present invention. For example, if the disclosure describes a first feature formed on or above a second feature, that is, it may involve an embodiment in which the first feature contacts with the second feature directly, and may also involve an embodiment in which additional features are formed between the first feature and the second feature, so that the first feature and the second feature are not in direct contact with each other. In addition, different embodiments of the following description may use the same reference symbols and/or labels. These repetitions are for the purpose of simplicity and clarity and are not intended to limit specific relationships between the different embodiments and/or structures.

Figure 1A:
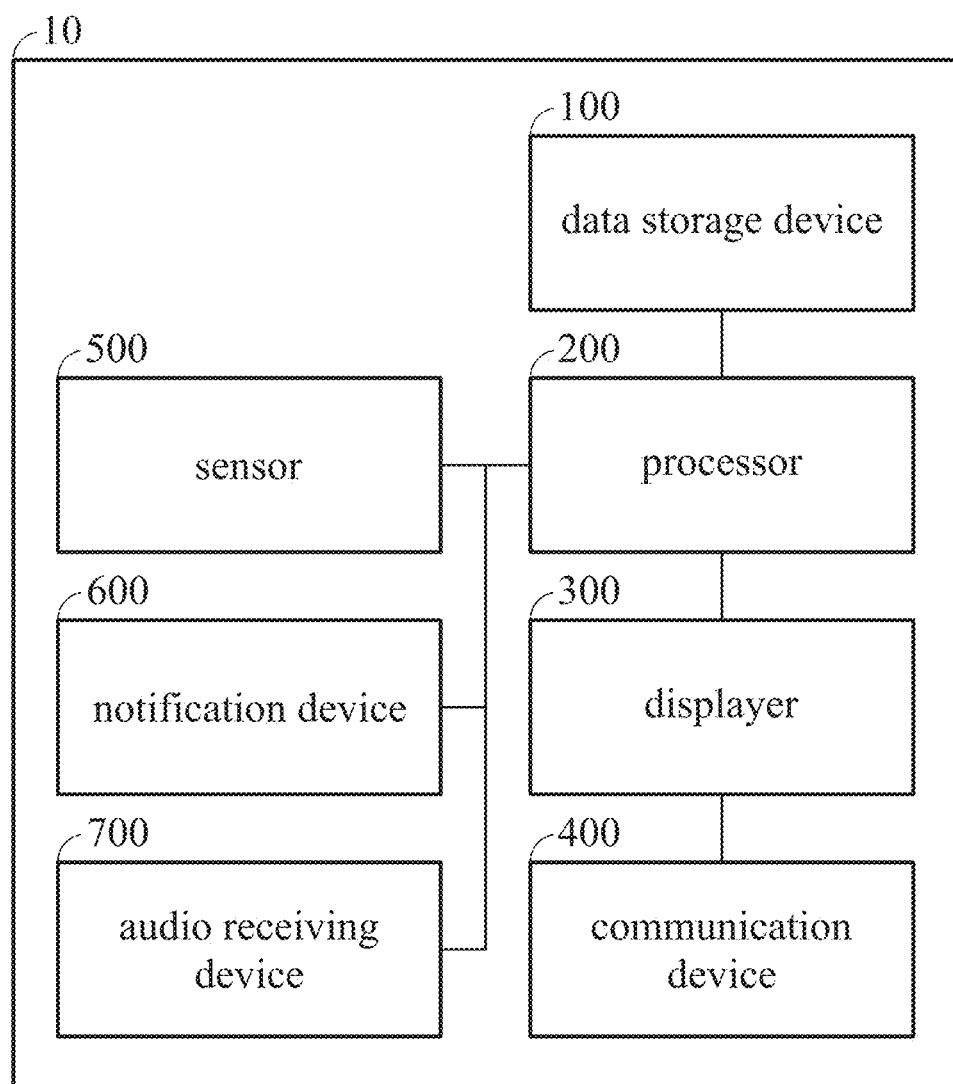
FIG. 1A is a schematic diagram showing an image detection device according to an exemplary embodiment of the present invention.

FIG. 1A is a schematic diagram showing an image detection device according to an exemplary embodiment of the present invention. The image detection device 10 comprises a data storage device 100, a processor 200, a displayer 300, a communication device 400, a sensor 500, a notification device 600, and an audio receiving device 700. The image detection device 10 can be an independent electronic device or built in a mobile electronic device (such as a mobile phone, a tablet computer, a notebook computer, a game device, an e-book or a PDA), a desktop computer, a server, or any electronic device equipped with a touch module (for example, a touch integrated circuit). The data storage device 100 can comprise storage units and can be implemented by a random access memory (RAM), a read only memory (ROM), a flash memory (Flash), a hard disk, a floppy disk, a magnetic memory, an optical disc (CD), a digital video disc (DVD), etc.

Moreover, the processor 200 of the image detection device 10 is coupled to the data storage device 100 for accessing the data in the data storage device 100. The processor 200 can comprise a digital signal processing (DSP), a microprocessor (MCU), a single central processing unit (CPU), or a plurality of parallel processing units related to a parallel processing environment for executing an operation system, modules, and applications. The displayer 300 is used to display the data in the data storage device 100. The displayer 300 can be, for example, a projection displayer, a stereoscopic imaging displayer, an organic light-emitting diode displayer, an electronic paper, a system integrated panel, a light-emitting diode displayer, a liquid crystal screen, or a touch display panel, such as a resistive touch panel, a capacitive touch panel, an optical touch panel, or an electromagnetic touch panel. The audio receiving device 700 is a device, such as a microphone, for receiving the user's voice.

The communication device 400 supports a wireless communication protocol for data transmission with another electronic device. For example, the wireless communication protocol may comprise GSM, GPRS, EDGE, UMTS, W-CDMA, CDMA2000, TD-CDMA, Bluetooth, NFC, WiFi, Wi-Fi Direct, WiMAX, LTE, LTE-A, or TD-LTE. The sensor 500 is configured to receive an optical signal, convert the optical signal into an electrical signal such as a pixel, and transmit the electrical signal to the processor 200 for calculation. For example, the sensor 500 may comprise an active pixel sensor (APS), a CMOS image sensor, a photosensitive coupling element (CCD), an infrared sensing element, a phototransistor, various optical lenses, or the like. Therefore, the image of the user can be detected by the sensor 500 even in a dim or dark environment. The notification device 600 is configured to play sound or emit light when the processor 200 determines that the user is in a dangerous position, for example, when the processor 200 determines that the user is sleeping in the prone position, to notify the other person of the dangerous position of the user, thereby achieving the purpose of caring for the user. For example, the notification device 600 may comprise an alarm, a buzzer, a warning light, a flasher, or an acousto-optic horn, or the like. In another embodiment, the notification device 600 transmits or pushes a warning message to the electronic device held by the user's family through the communication device 400 in the wireless transmission. For example, the warning message may be a text message or a voice message. Moreover, the electronic device held by the user's family may also be pre-installed with a software application (app) for receiving the warning message and receiving the images of the user.

Figure 1B:
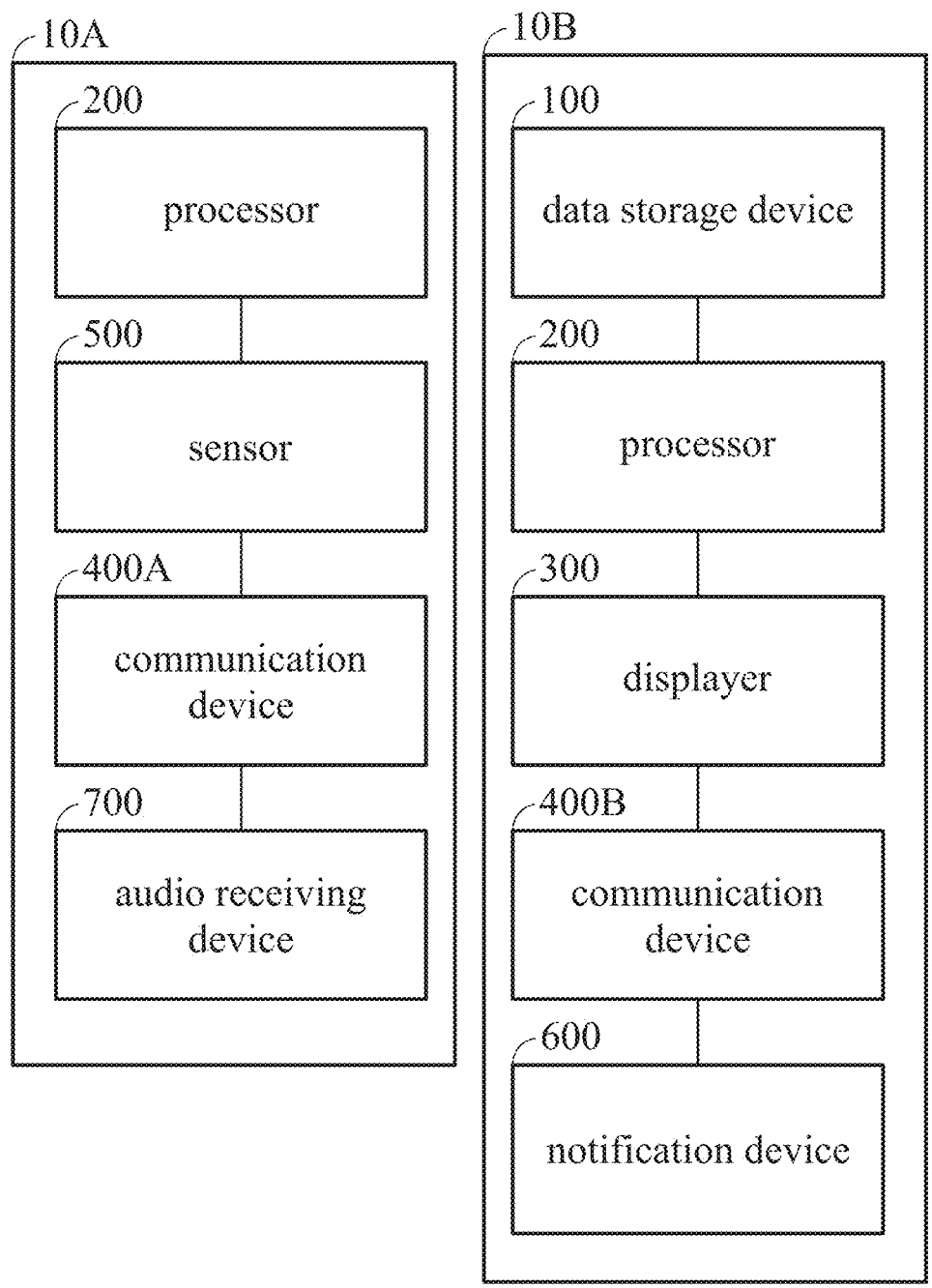
FIG. 1B is a schematic diagram showing an image detection device according to another exemplary embodiment of the present invention.

FIG. 1B is a schematic diagram showing an image detection device 10 according to another exemplary embodiment of the present invention. In this embodiment, the image detection device 10 is implemented by a separate design, that is, the image detection device 10 is composed of two image detection devices 10A and 10B. The two image detection devices 10A and 10B connect to and communicate with each other in a wire or wireless manner. The image detection device 10A comprises a processor 200, an audio receiving device 700, a sensor 500, and a communication device 400A. The image detection device 10B comprises a data storage device 100, a processor 200, a displayer 300, a communication device 400B, and a notification device 600. The notification device 600 can be disposed in the image detection device 10A. The present invention does not intend to limit the position of the notification device 600 in the image detection device 10.

In detail, the image detection device 10A is installed in an environment in which the user is located (for example, a bedroom), and the image detection device 10B serves as a host. For example, the image detection device 10B can be a server, a mainframe, or a cloud host of the manufacturer of the image detection device 10. The images sensed by the sensor 500 of the image detection device 10A are transmitted to the image detection device 10B through the communication devices 400A and 400B for analysis.

In one embodiment, the sensor 500 is configured to capture a plurality of images of a user. The processor 200 determines whether the user moves according to the images and obtains a plurality of feature parameters of the images. In detail, the processor 200 calculates pixels included in each of the images, performs a subtraction operation on each set of two adjacent images to obtain a pixel difference, and then determines whether the user moves according to the pixel difference. If the pixel difference is greater than a predetermined pixel value, the processor 200 determines that the user has moved; if the pixel difference is less than or equal to the predetermined pixel value, the processor 200 determines that the user has not moved.

Then, the processor 200 performs a body distribution analysis and a face occlusion analysis on the images according to the feature parameters to determine the position of the user. For example, the feature parameters comprise the user's torso, face, head, eyes, nose, mouth, ears, hands, feet, and the distance between the center of the user's face and the center of the user's head. The face occlusion analysis is performed by using the user's eyes, nose, and mouth as the feature parameters to determine whether a face occlusion status has occurred on the user. In addition, the body distribution analysis is used to determine the position of the user and whether the user is sleeping in the supine position, on either side, in the prone position, or in another sleeping position.

Figure 1C:
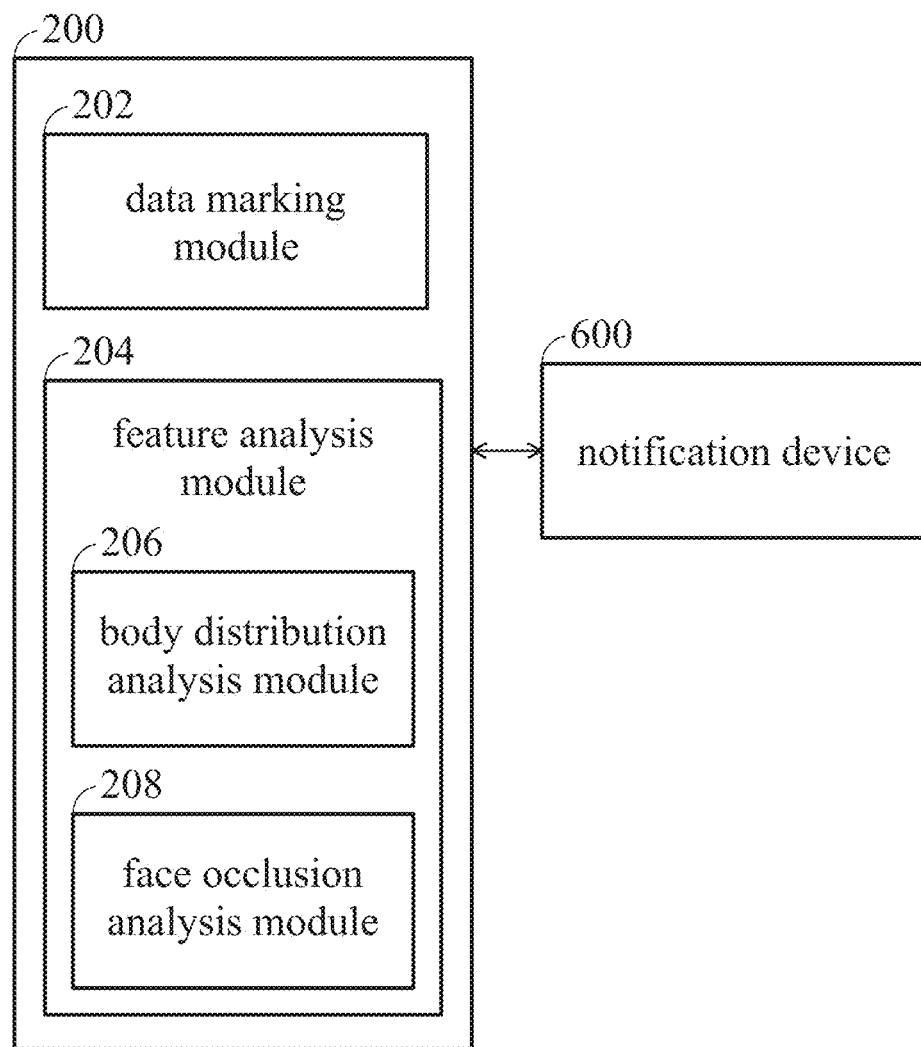
FIG. 1C is a schematic diagram showing a processor and a notification device according to another exemplary embodiment of the present invention.

FIG. 1C is a schematic diagram showing the processor 200 and the notification device 600 according to another exemplary embodiment of the present invention. The processor 200 comprises a data marking module 202 and a feature analysis module 204. The data marking module 202 marks a plurality of feature parameters in the images captured by the sensor 500. The feature analysis module 204 is configured to calculate and analyze the detection result related to the feature parameters in each image. For example, the feature analysis module 204 determines whether the user's nose is occulted or calculates the distance between the center of the user's face and the center of the user's head.

In addition, the feature analysis module 204 comprises a body distribution analysis module 206 and a face occlusion analysis module 208 for performing the body distribution analysis and the face occlusion analysis, respectively. The feature parameters used for body distribution analysis may be different from the feature parameters used for the face occlusion analysis. In an embodiment, the processor 200 first analyzes the feature parameters of the user by using the body distribution analysis module 206 and then uses the face occlusion analysis module 208 to analyze the feature parameters of the user to accurately determine the position and face occlusion status of the user.

If the confidence level of the above analysis is lower than a predetermined confidence value, it indicates that the reliability of the analysis is insufficient, and the processor 200 will not adopt the result of the body distribution analysis. At this time, the processor 200 determines the position of the user through the face occlusion analysis module 208. If the confidence value of the above analysis is higher than or equal to the predetermined confidence value, it indicates that the reliability of the analysis is sufficient, and the processor 200 will use the result of the body distribution analysis and perform the auxiliary determination through the face occlusion analysis. Therefore, the double analyses related to the body distribution and face occlusion can improve the accuracy of the determination of the position of the user.

In other words, the body distribution analysis module 206 performs the body distribution analysis based on the detection results of the feature parameters and initially determines the position of the user (i.e., the first position information). Then, the face occlusion analysis module 208 performs the face occlusion analysis on the images according to the detection results of the feature parameters and the first position information to obtain the second position information of the user. It should be noted that the second position information may be different from the first position information, and the second position information represents the final determination result of the position of the user.

Figure 2:
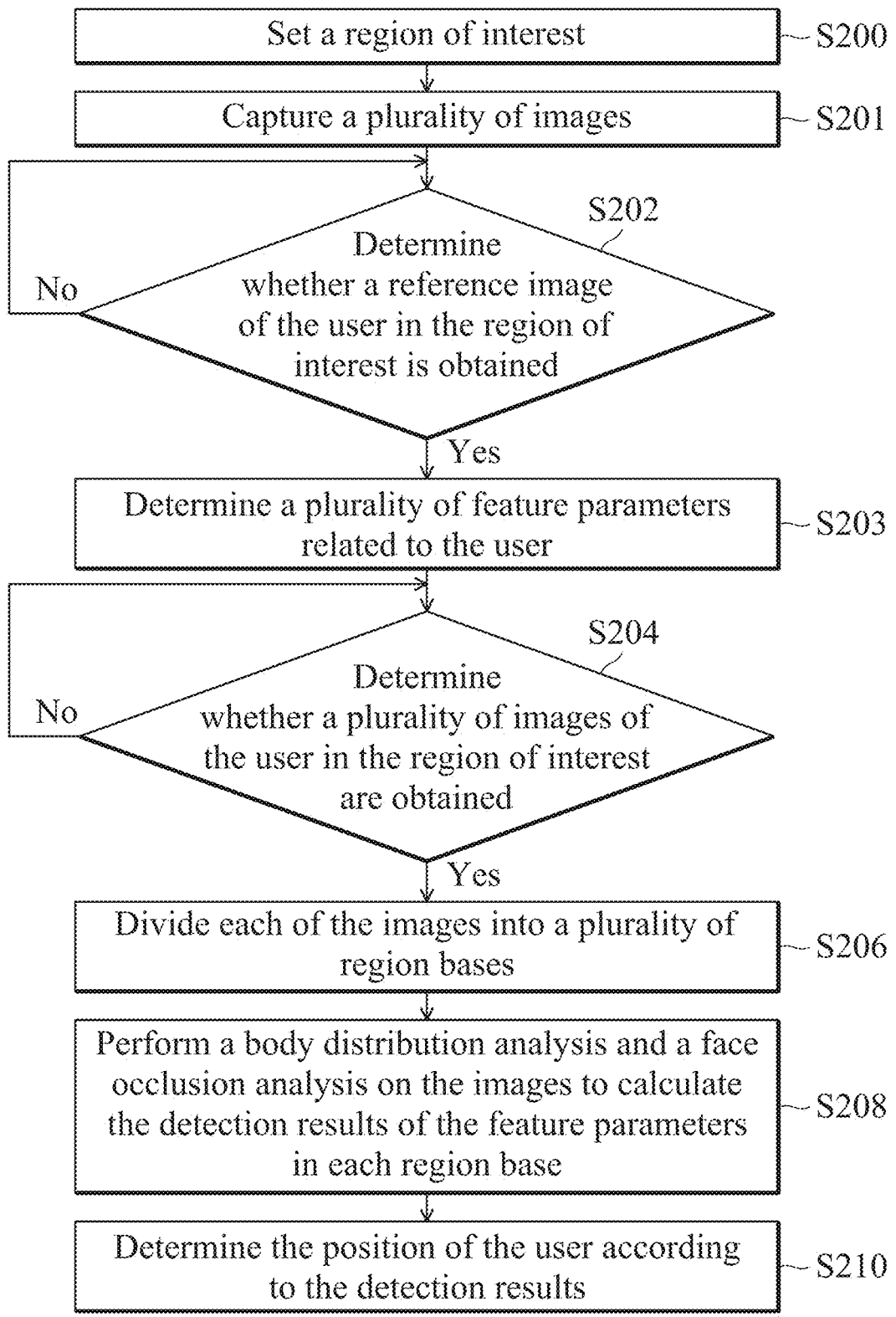
FIG. 2 is a flow chart showing an image detection method according to an exemplary embodiment of the present invention.

FIG. 2 is a flow chart showing an image detection method according to an exemplary embodiment of the present invention. In step S200, the processor 200 activates the image detection device 10 and sets a region of interest (ROI). In an embodiment, the image detection device 10 is used to determine the sleeping position of the user, and thus the region of interest ROI is set as the bed where the user lies. The region of interest ROI may be preset by the image detection device 10 or may be set by the user according to the environment. When the setting is complete, in step S201, the sensor 500 starts shooting to capture a plurality of images related to the user. For example, the sensor 500 takes 10~30 images per second to record and detect the position of the user in the ROI. The number of images captured by the sensor 500 per second is for illustrative purposes only and is not intended to limit the invention. In detail, the sensor 500 can adjust the number of images captured per second according to the user environment and the needs of the user. For example, when the user needs to increase the accuracy of the determination, the number of images captured by the sensor 500 per second can be increased.

In step S202, the processor 200 determines whether a first image is obtained. In detail, the processor 200 defines the first image as a reference image which is a comparison reference for determining the position of the user. In step S203, the processor 200 determines a plurality of feature parameters related to the user. Then, in step S204, the processor 200 determines whether a plurality of images of the user in the region of interest are obtained. In detail, when the sensor 500 captures other images other than the reference image, the processor 200 performs a subtraction operation on the other images and the reference image to obtain a difference and determines whether the user moves.

Then, in step S206, the processor 200 divides each of the above images into a plurality of region bases. In step S208, the processor 200 performs the body distribution analysis and face occlusion analysis on the images to calculate the detection results of the feature parameters in each region base. Finally, in step S210, the processor 200 determines the position of the user according to the detection results.

Figure 3:
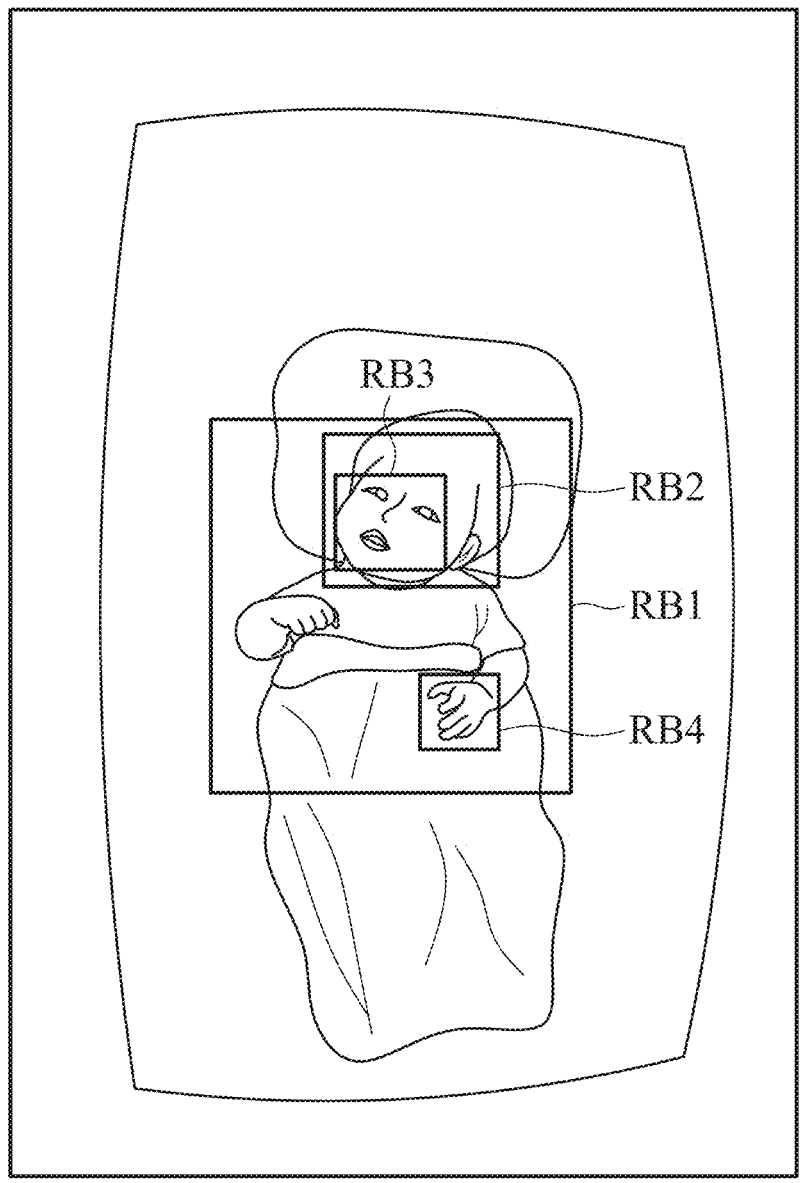
FIG. 3 is a schematic diagram showing a plurality of region bases according to an exemplary embodiment of the present invention.

FIG. 3 is a schematic diagram showing a plurality of region bases according to an exemplary embodiment of the present invention. The feature analysis module 204 of the processor 200 divides the image of the user into a plurality of region bases RB1~RB4. As shown in FIG. 3, the region base RB1 corresponds to the user's body, the region base RB2 corresponds to the user's head, the region base RB3 corresponds to the user's face, and the region base RB4 corresponds to the user's hand.

Then, the feature analysis module 204 analyzes the detection results of the feature parameters in each of the region bases RB1~RB4. The feature parameters include the user's torso, face, head, eyes, nose, mouth, ears, hands, feet, and the distance between the center of the user's face and the center of the user's head. Therefore, the feature analysis module 204 can detect and determine whether the feature parameters appear in the region bases RB1~RB4.

In detail, the feature analysis module 204 comprises the body distribution analysis module 206 and the face occlusion analysis module 208. For example, the body distribution analysis module 206 belongs to the human body feature extraction model which is a region-based convolutional neural network (CNN) for identifying the features of each region base. In order to reduce the amount of data calculation and increase the speed, the present invention adopts feature sharing between a region generation network (RPN) and a feature extraction network to simultaneously divides the region bases and extracts feature parameters. Furthermore, the above-mentioned human body feature extraction model can also use a deep residual network (ResNet) as a feature extraction network to reduce the memory usage and improve the efficiency of the feature extraction.

Figure 4A:
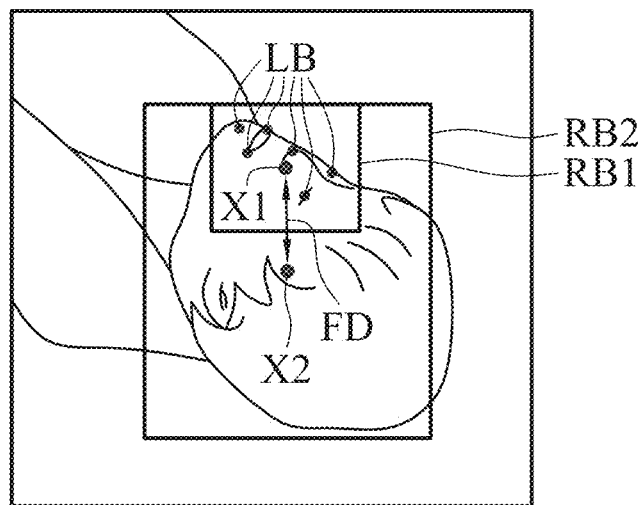
FIGS. 4A and 4B are schematic diagrams showing marking of feature parameters according to an exemplary embodiment of the present invention.
Figure 4B:
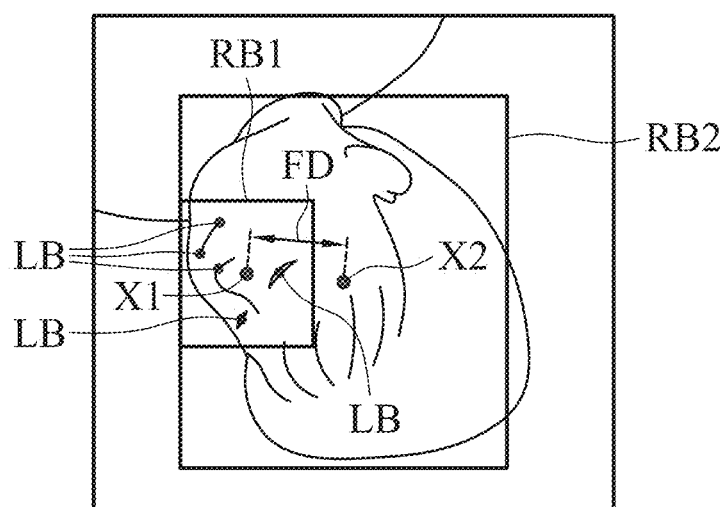

FIGS. 4A and 4B are schematic diagrams showing marking of feature parameters according to an exemplary embodiment of the present invention. In an embodiment, the data marking module 202 of the processor 200 marks feature parameters such as the user's face or facial feature from the image data collected by the sensor 500. Then, according to the feature parameters marked by the data marking module 202, the feature analysis module 204 determines the position of the user and further determines whether a face occlusion status occurs.

First, a feature such as the user's face or a facial feature is manually marked in the image using a label. Through the learning, training and evaluation of the neural network, the data marking module 202 can automatically and intelligently mark the feature parameters in an image. After the marking is complete, the corresponding script is automatically built in the training database and the evaluation database.

As shown in FIGS. 4A and 4B, the image of the user includes two regional bases RB1 and RB2 representing the user's face and head respectively, wherein the center point of the face is represented as X1, and the center point of the head is represented as X2. The data marking module 202 then marks the eyes, nose, mouth, and the like with labels LB. The feature analysis module 204 extracts various feature parameters according to the labels LB, such as the user's torso, face, head, eyes, nose, mouth, ears, hands, feet, the distance FD between the center of the user's face and the center of the user's head, and so on. If the distance FD between the center of the user's face and the center of the user's head is short, it means that the user is in a frontal-face position (i.e., the face is facing upwards); if the distance FD between the center of the user's face and the center of the user's head is greater, it means the user is in a lateral-face position.

Figure 5:
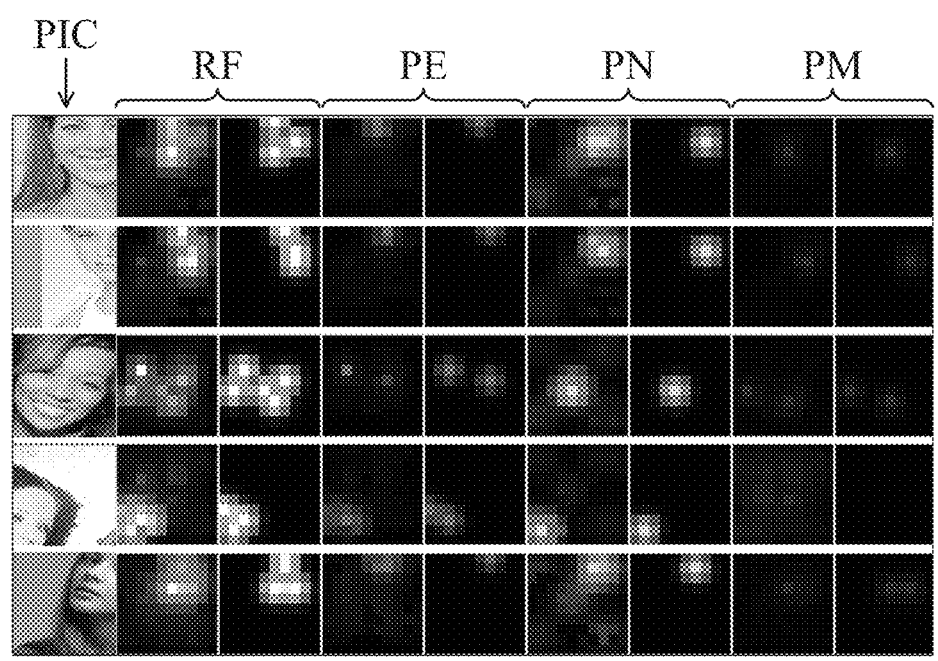
FIG. 5 is a schematic diagram showing feature parameters being obtained from an image of the user according to an exemplary embodiment of the present invention.

FIG. 5 is a schematic diagram showing feature parameters being obtained from an image of the user according to an exemplary embodiment of the present invention. The feature analysis module 204 provided in the present application comprises the body distribution analysis module 206 and a face occlusion analysis module 208. The face occlusion analysis module 208 can be an occlusion determination model which comprises neural networks for two stages. The first-stage neural network comprises three lightweight mobile networks (MobileNet) that perform training respectively for the user's eyes, nose and mouth to accurately determine the positions of the user's eyes, nose and mouth as three feature parameters.

Moreover, the second-stage neural network is a fully connected network. The second-stage neural network receives the feature parameters extracted by the first-stage neural network and performs evaluation and training related to whether the occlusion status occurs.

In addition, the body distribution analysis module 206 and the face occlusion analysis module 208 described in the present invention can be developed based on the Tensorflow application framework or other deep learning application frameworks and further use a graphics processing unit (GPU) to achieve effect of accelerated operations. As shown in FIG. 5, by using the feature analysis module 204 described in the present invention, the feature parameter PF of the face, the feature parameter PE of the eyes, the feature parameter PN of the nose, and the feature parameter PM of the mouth can be extracted for each of the various images PIC. Then, the face occlusion analysis module 208 determines whether the occlusion status occurs for each of the feature parameters.

In another embodiment, the processor 200 may, according to the feature parameters, determine whether the image clearly shows the user's face, and it may also determine a plurality of feature vectors in order to determine the body position and the position type of the user. Then, the processor 200 selects a representative image related to a certain position type according to the above determination results. The communication device 400 transmits the representative image to the user's family, relatives, or friends.

Figure 6A:
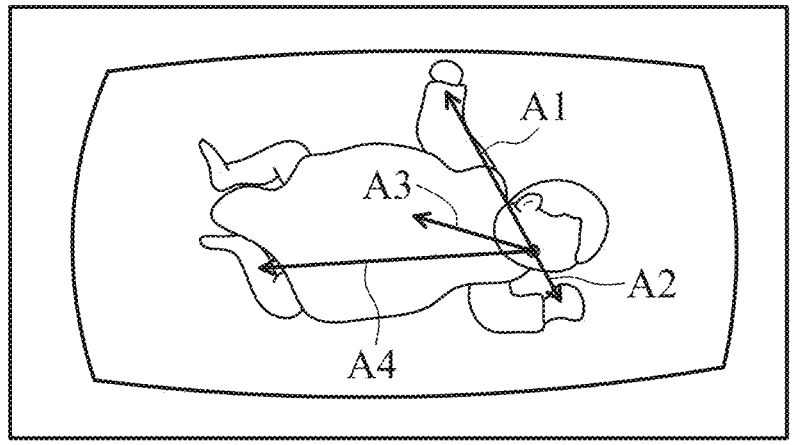
FIGS. 6A and 6B are schematic diagrams showing feature vectors according to an exemplary embodiment of the present invention.
Figure 6B:
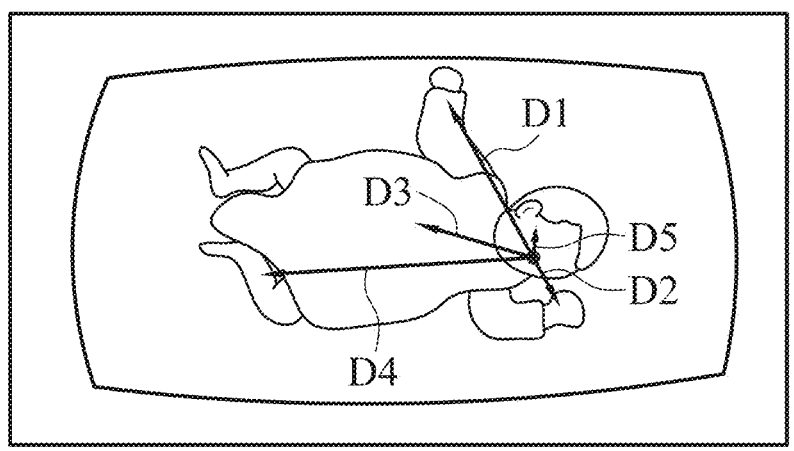

For example, the feature vectors include the user's voice, the angles between the user's face and hands, the distances between the face and the hands, the angles between the user's face and the feet, and the distances between the face and the feet. The user's voice as received by the audio receiving device 700 may indicate laughter or crying. Therefore, the processor 200 can determine the state and mood of the user according to the user's voice and determine the body position and position type through the combination of using the body distribution analysis and the face occlusion analysis. FIGS. 6A and 6B are schematic diagrams showing feature vectors according to an exemplary embodiment of the present invention. As shown in FIG. 6A, the image includes four feature vectors, which are the angle A1 between the user's face and right hand, the angle A2 between the user's face and left hand, the angle A3 between the user's face and right foot, and the angle A4 between the user's face and left foot, wherein the angle A1 is about 297 degrees, the angle A2 is about 123 degrees, the angle A3 is about 343 degrees, and the angle A4 is about 4 degrees.

In addition to the angles, distances can also be used as feature vectors, and then different position types of the user can be distinguished. As shown in FIG. 6B, the image includes five feature vectors, which are the distance D1 between the user's face and right hand, the distance D2 between the user's face and left hand, the distance D3 between the user's face and right foot, the distance D4 between the user's face and left foot, and the distance D5 between the user's face and head, wherein the distance D1 is about 358 pts (pixel), the distance D2 is about 99 pts, the distance D3 is about 250 pts, the distance D4 is about 500 pts, and the distance D5 is about 45 pts.

In an embodiment, the processor 200 sets a predetermined number of position types. First, the processor 200 determines whether one image clearly shows the user's face. If yes, the processor 200 determines the position type to which the image belongs according to the above feature vectors and the results of the body distribution analysis and the face occlusion analysis. Then, for each of the position types, the image in which the distance between the center of the face and the center of the head is shortest is selected as the representative image for the determined position type. In addition, the processor 200 periodically selects a representative image of each of the position types. For example, one representative image may be selected per day, or one representative image may be selected every morning and evening.

Figure 7:
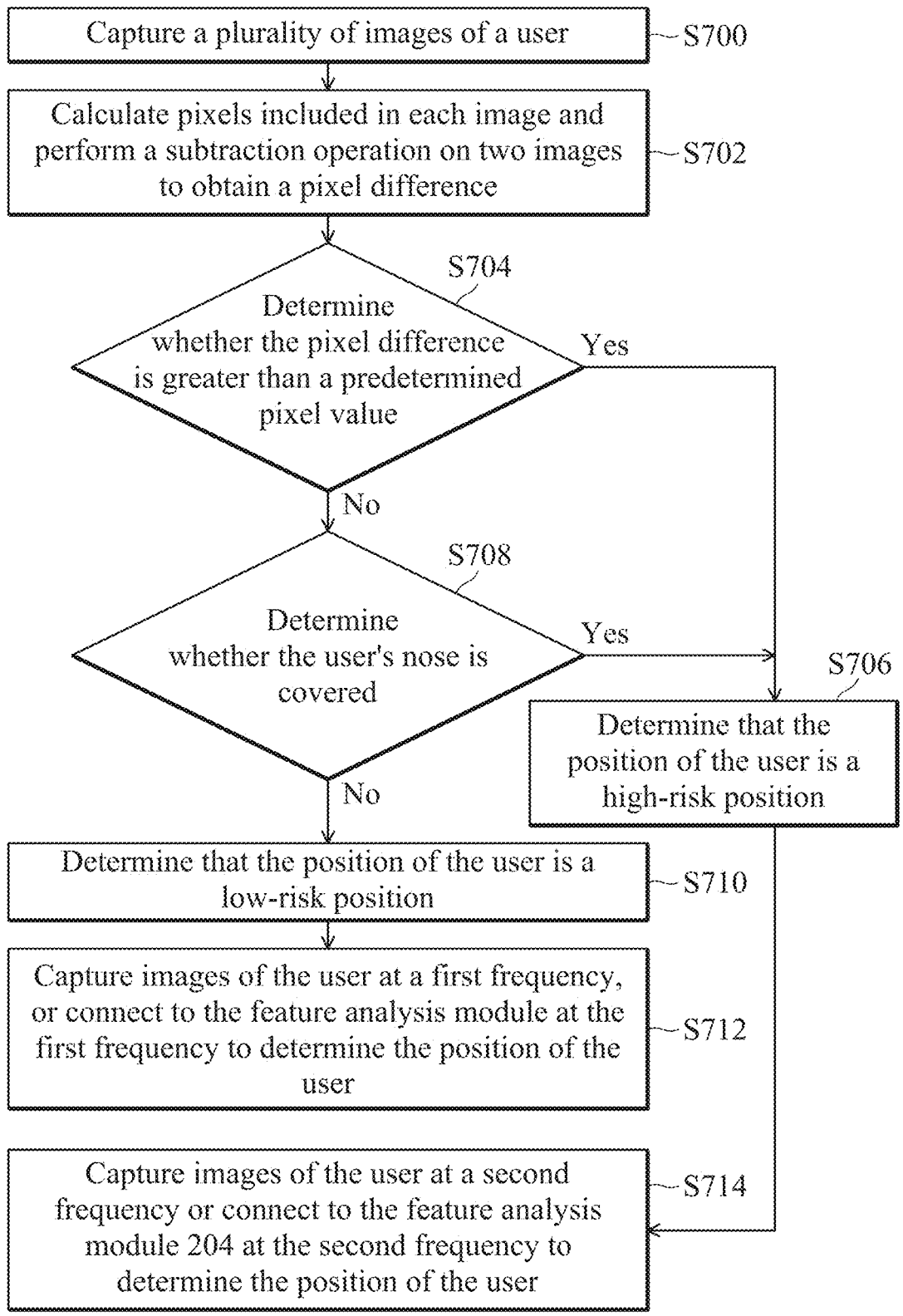
FIG. 7 shows a flow chart of determination of a risk from images according to an risk embodiment of the invention.

FIG. 7 shows a flow chart of determination of a risk from images according to an exemplary embodiment of the present invention. In Step S700, the sensor 500 captures a plurality of images of a user. In Step S702, the processor 200 calculates pixels included in each image and performs a subtraction operation on two images to obtain a pixel difference. In Step S704, the processor 200 determines whether the pixel difference is greater than a predetermined pixel value. If the pixel difference is greater than the predetermined pixel value, Step S706 is performed. In Step S706, the processor 200 determines that the position of the user is a high-risk position. If the pixel difference is less than or equal to the predetermined pixel value, Step S708 is performed. In Step S708, the processor 200 determines whether the user's nose is covered.

If the user's nose user is not covered, Step S710 is performed. In Step S710, the processor 200 determines that the position of the user is a low-risk position. Then, in Step S712, the sensor 500 captures images of the user at a first frequency, or connects to the feature analysis module 204 at the first frequency to determine the position of the user. If the nose of the user is covered, Step S706 is performed. In Step S706, the processor 200 determines that the position of the user is a high-risk position. Next, in Step S714, the sensor 500 captures images of the user at a second frequency or connects to the feature analysis module 204 at the second frequency to determine the position of the user. The second frequency is higher than the first frequency. Therefore, when the high-risk position is determined, the image detection device 10 of the present invention captures images and determines the position of the user at a higher frequency, thereby accurately detecting the position of the user early to prevent danger.

Figure 8:
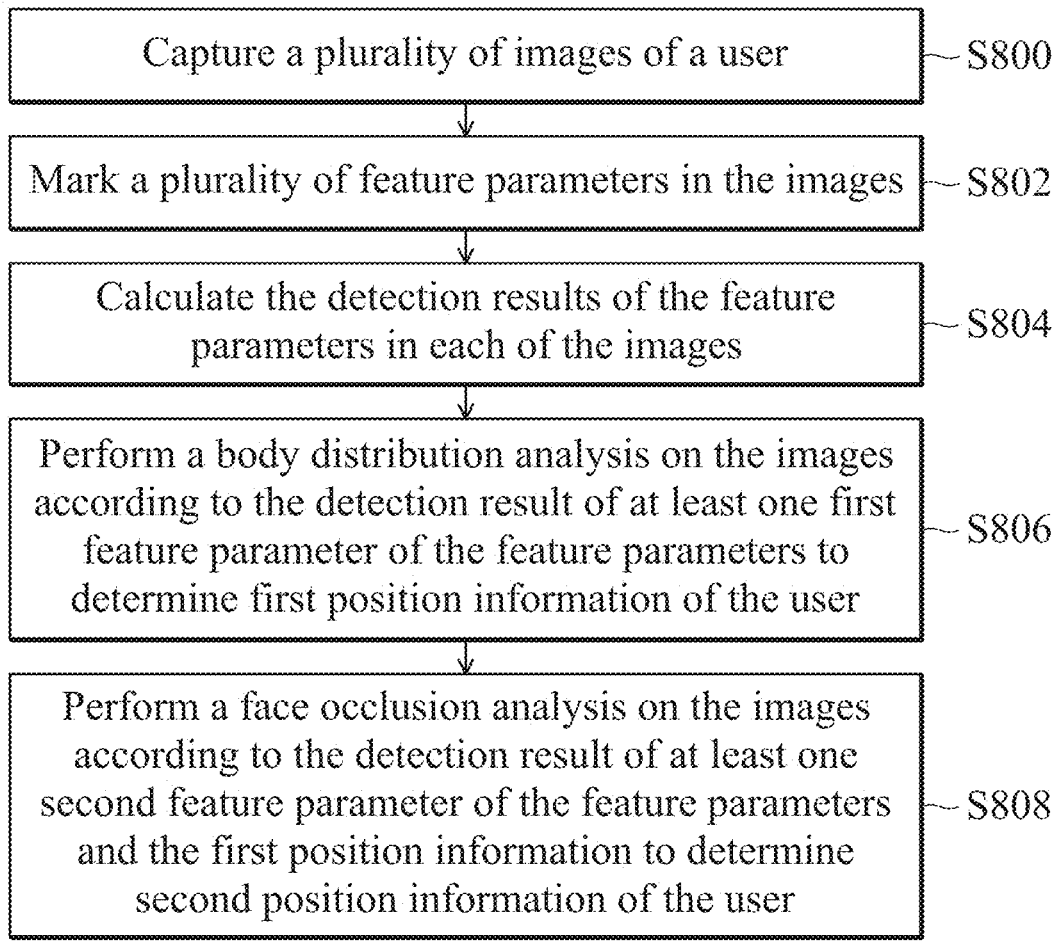
FIG. 8 shows a flow chart of a body distribution analysis and a face occlusion analysis according to an exemplary embodiment of the present invention.
Figure 9A:
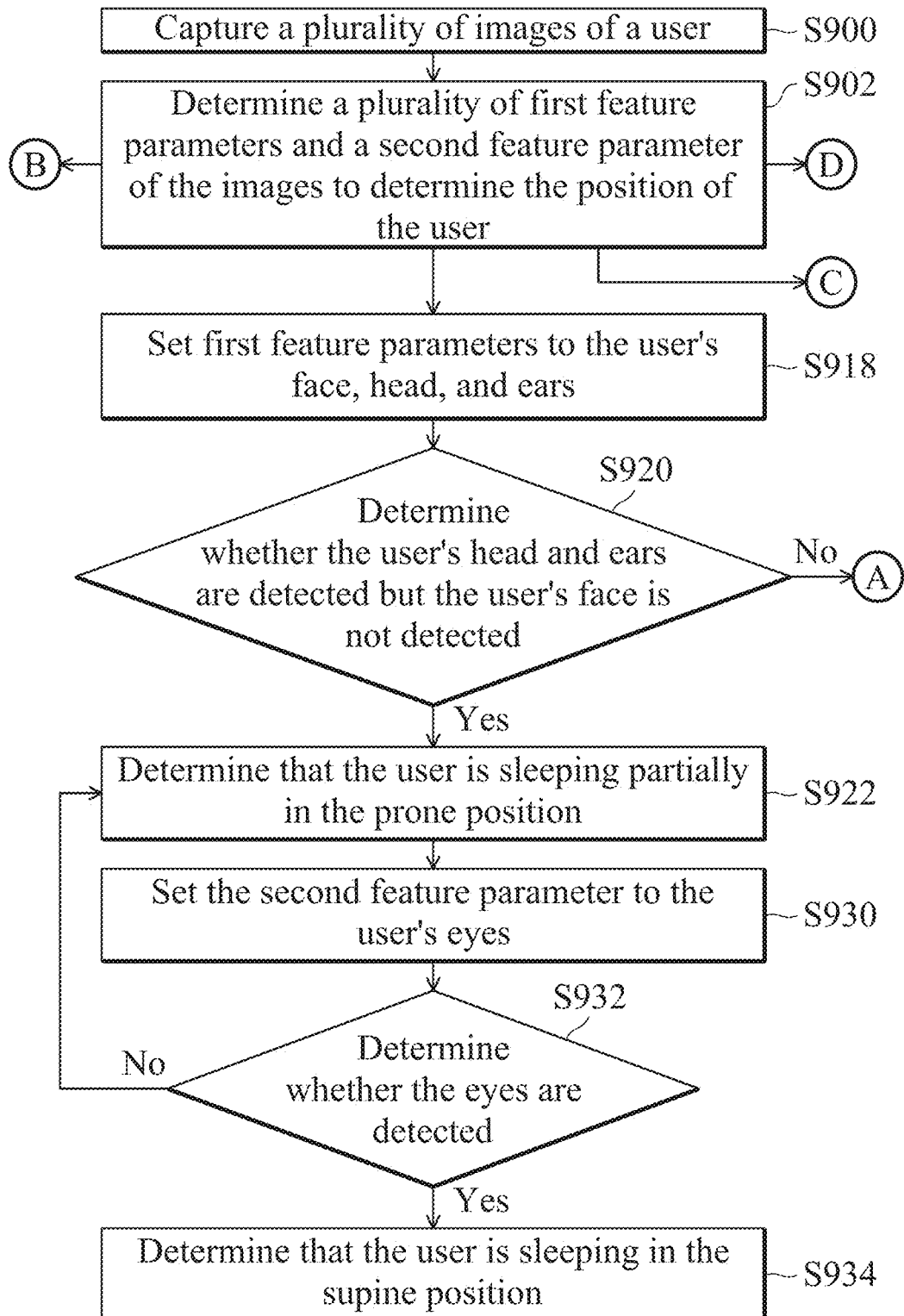
FIGS. 9A-9E show a flow chart of determination of a position of the user according to a collaborative body distribution analysis and a face occlusion analysis according to an exemplary embodiment of the present invention.
Figure 9B:
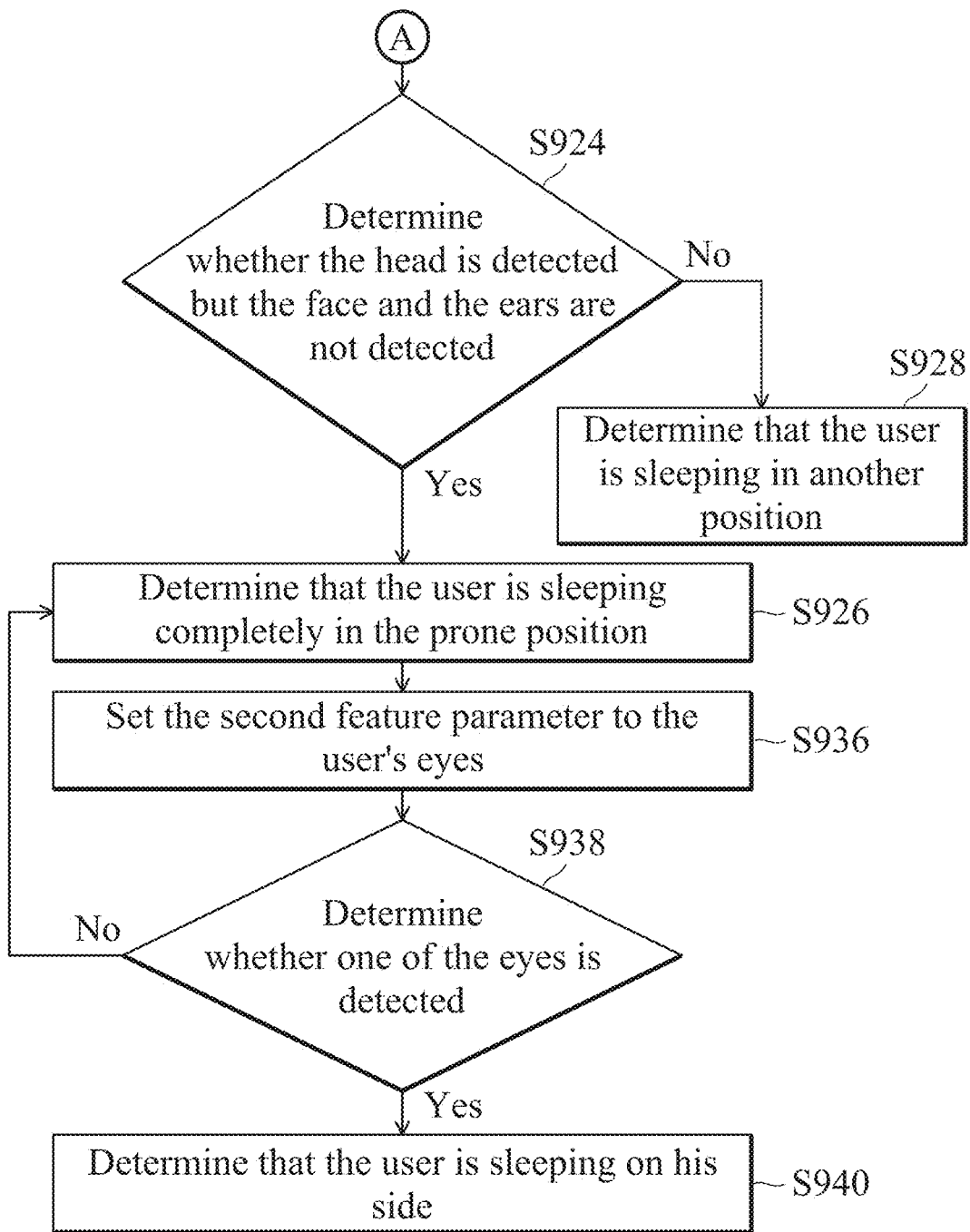
Figure 9C:
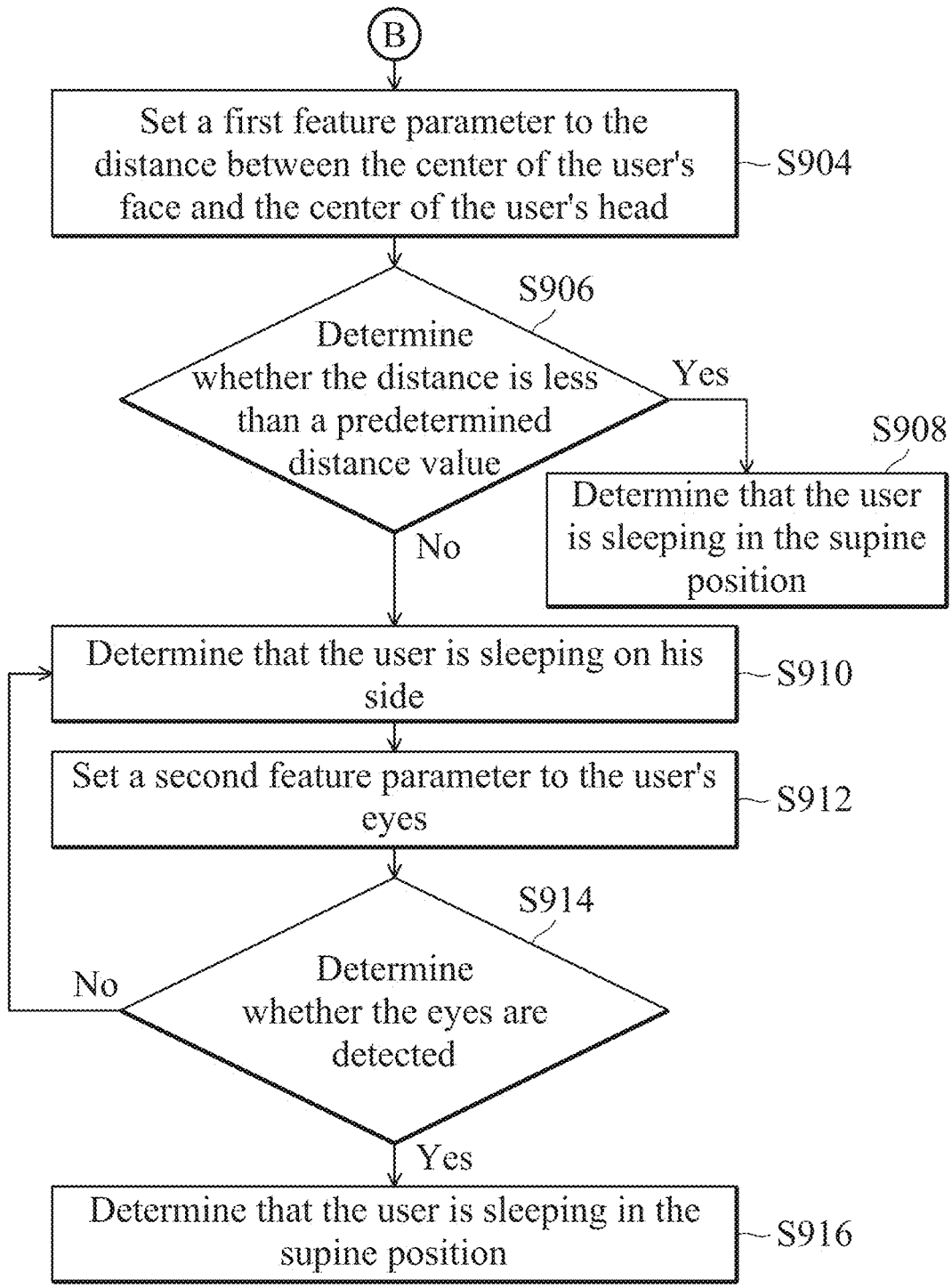
Figure 9D:
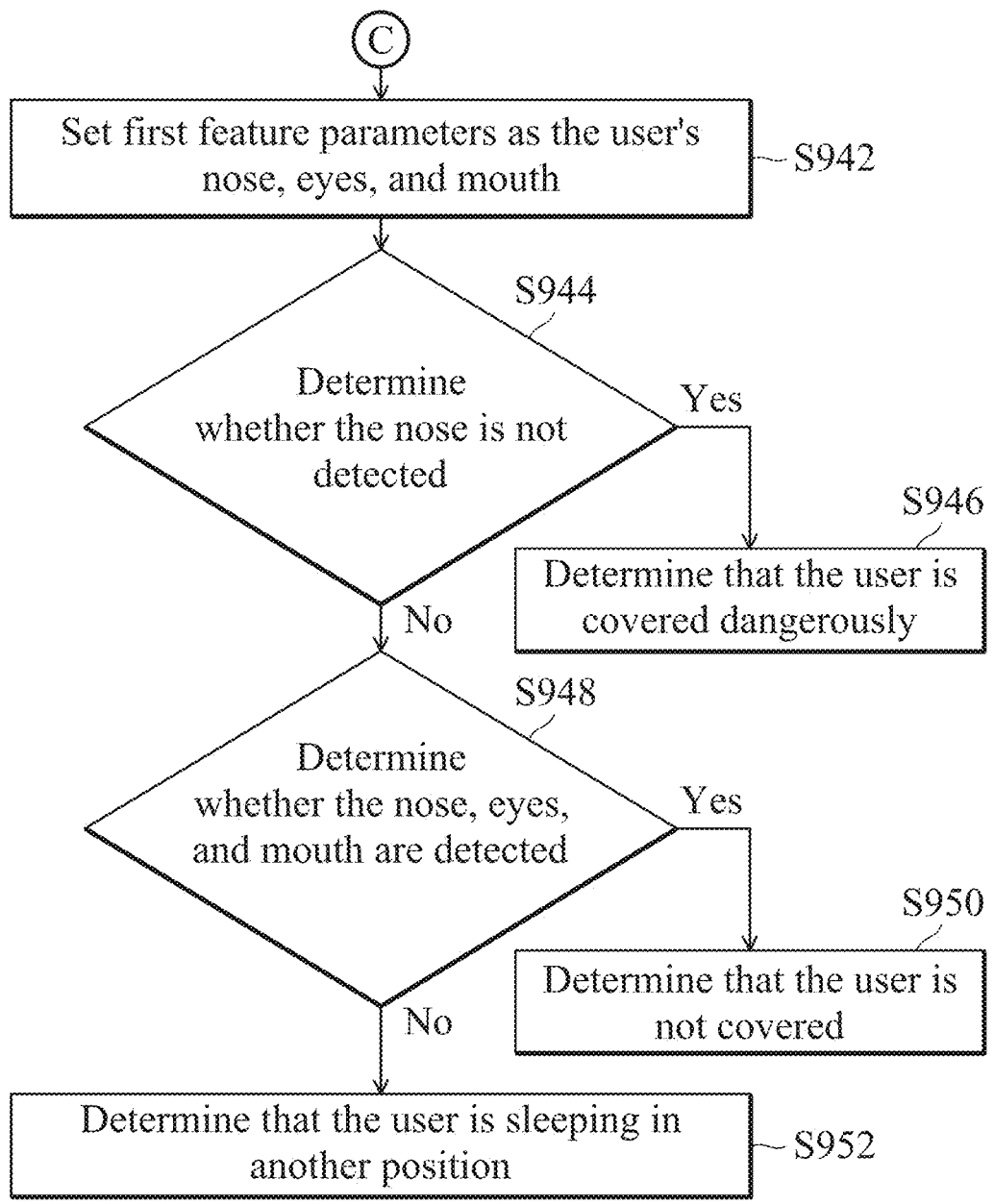
Figure 9E:
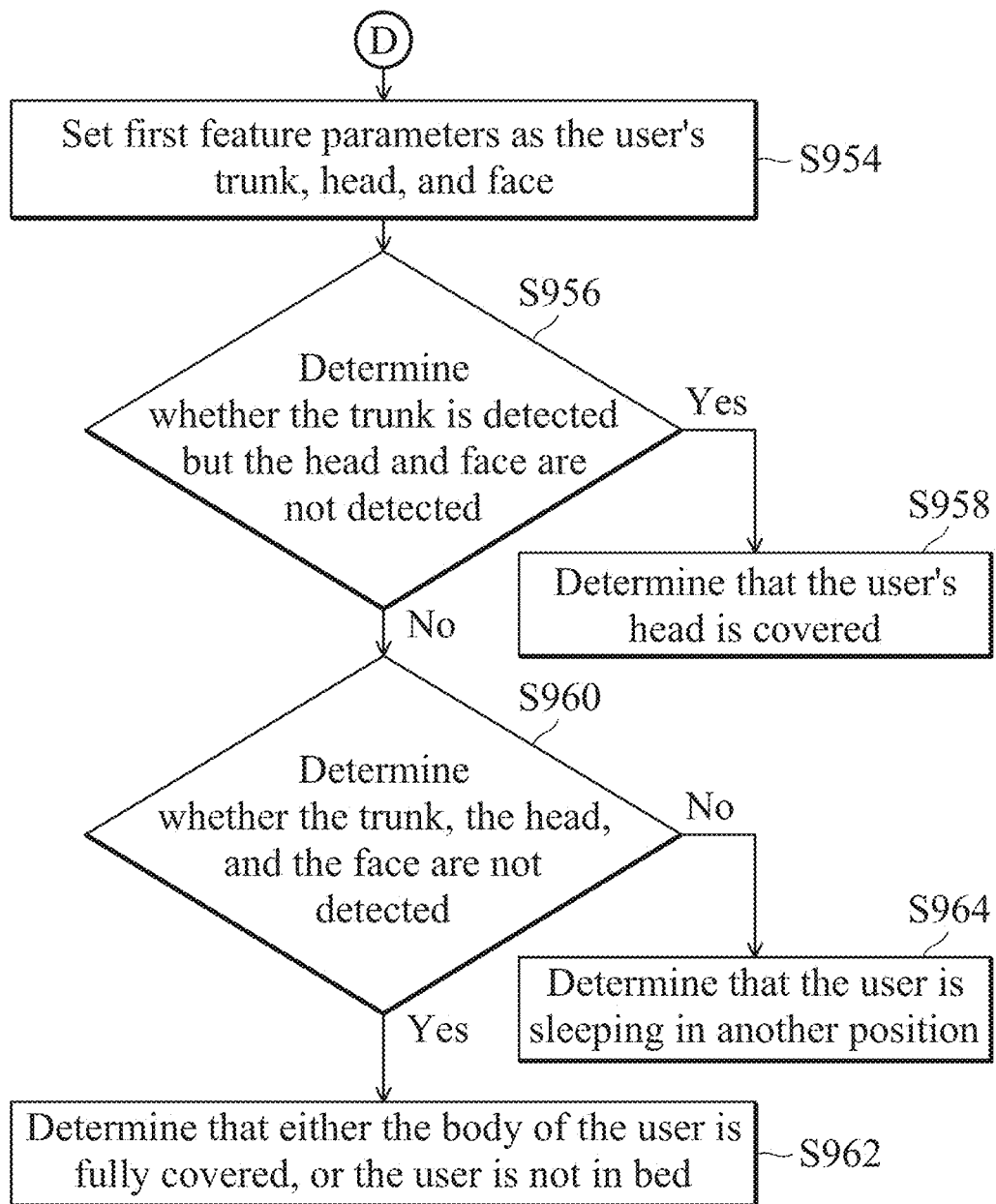

FIG. 8 shows a flow chart of a body distribution analysis and a face occlusion analysis according to an exemplary embodiment of the present invention. Performing two different analyses, a body distribution analysis and a face occlusion analysis, can effectively improve the accuracy of the determination of the position of the user. In Step S800, the sensor 500 captures a plurality of images of a user. In Step S802, the data marking module 202 marks a plurality of feature parameters in the images. In Step S804, the processor 200 calculates and evaluates the detection results of the feature parameters in each of the above images.

Next, in step S806, the processor 200 performs a body distribution analysis on the images according to the detection result of at least one first feature parameter of the feature parameters to determine first position information of the user. It should be noted that in order to improve the accuracy of the determination, the processor 200 may perform a face occlusion analysis to assist in determining the position of the user. In Step S808, the processor 200 performs a face occlusion analysis on the images according to the detection result of at least one second feature parameter of the feature parameters and the first position information to determine second position information of the user. Since the second position information is determined to correct the first position information, it can be used to determine the actual position of the user.

FIGS. 9A-9E show a flow chart of determination of a position of a user according to a body distribution analysis and a face occlusion analysis according to an exemplary embodiment of the present invention. In Step S900, the sensor 500 captures a plurality of images of a user. In Step S902, the processor 200 determines a plurality of first feature parameters and a second feature parameter of the images to determine the position of the user. Depending on the selected first feature parameter, Step S904, Step S918, Step S942, or Step S954 may be performed next, which will be described separately in the following paragraphs.

In Step S904, the processor 200 sets a first feature parameter to the distance between the center of the user's face and the center of the user's head. In Step S906, the processor 200 determines whether the distance is less than a predetermined distance value. For example, the above predetermined distance value is 60 pts. If the distance is less than the predetermined distance value, Step S908 is performed. In Step S908, the processor 200 determines that the user is sleeping in the supine position. If the distance is greater than or equal to the predetermined distance value, Step S910 is executed. In Step S910, the processor 200 determines that the user is sleeping on his side.

Then, in Step S912, the processor 200 sets a second feature parameter to the user's eyes. In Step S914, the processor 200 determines whether both of the eyes are detected at the same time. If both of the eyes are detected, Step S916 is performed. In Step S916, the processor 200 determines that the user is sleeping in the supine position. If both of the eyes are not detected at the same time, Step S910 is performed. In Step S910, the processor 200 determines that the user is sleeping on his side.

In another embodiment, as shown in Step S918, the processor 200 sets first feature parameters to the user's face, head, and ears. In Step S920, the processor 200 determines whether the user's head and ears are detected but the user's face is not detected. If yes, the method proceeds to Step S922; if no, the method proceeds to Step S924.

In S922, the processor 200 determines that the user is sleeping partially in the prone position. Next, in Step S930, the processor 200 sets the second feature parameter to the user's eyes. In Step S932, the processor 200 determines whether both of the eyes are detected at the same time. If both of the eyes are detected, Step S934 is performed. In Step S934, the processor 200 determines that the user is sleeping in the supine position. If both of the eyes are not detected at the same time, Step S922 is performed. In Step S922, the processor 200 determines that the user is sleeping partially in the prone position.

In addition, in Step S924, the processor 200 determines whether the head is detected but the face and the ears are not detected. If no, the method proceeds to Step S928 in which the processor 200 determines that the user is sleeping in another position; if yes, the method proceeds to Step S926 in which the processor 200 determines that the user is sleeping completely in the prone position. Then, Step S936 is performed. In Step S936, the processor 200 sets the second feature parameter to the user's eyes. In Step S938, the processor 200 determines whether one of the eyes is detected. If yes, the method proceeds to Step S940 in which the processor 200 determines that the user is sleeping on his side; if no, the method proceeds to Step S926 in which the processor 200 determines that the user is sleeping completely in the prone position.

In another embodiment, as shown in Step S942, the processor 200 sets first feature parameters as the user's nose, eyes, and mouth. In Step S944, the processor 200 determines whether the nose is not detected. If yes, the method proceeds to Step S946 in which the processor 200 determines that the user is covered dangerously. At this time, the processor 200 transmits a warning message through the notification device 600 to notify the user's family, relatives, or caregivers of this face occlusion status; if no, the method proceeds to Step S948.

In Step S948, the processor 200 determines whether the nose, eyes, and mouth are detected. If the nose, eyes, and mouth are detected, the method proceeds to Step S950 in which the processor 200 determines that the user is not covered. Moreover, if the nose, eyes and mouth are not detected, the method proceeds to Step S952 in which the processor 200 determines that the user is sleeping in another position.

In another embodiment, as shown in Step S954, the processor 200 sets first feature parameters as the user's trunk, head, and face. In Step S956, the processor 200 determines whether the trunk is detected but the head and face are not detected. If yes, the method proceeds to Step S958 in which the processor 200 determines that the user's head is covered; if no, the method proceeds to Step S960.

In Step S960, the processor 200 determines whether the trunk, the head, and the face are not detected. If the trunk, head and face are not detected, the method proceeds to Step S962 in which the processor 200 determines that either the body of the user is fully covered, or the user is not in bed. If the trunk, the head and the face are detected, the method proceeds to Step S964 in which the processor 200 determines that the user is sleeping in another position.

Figure 10:
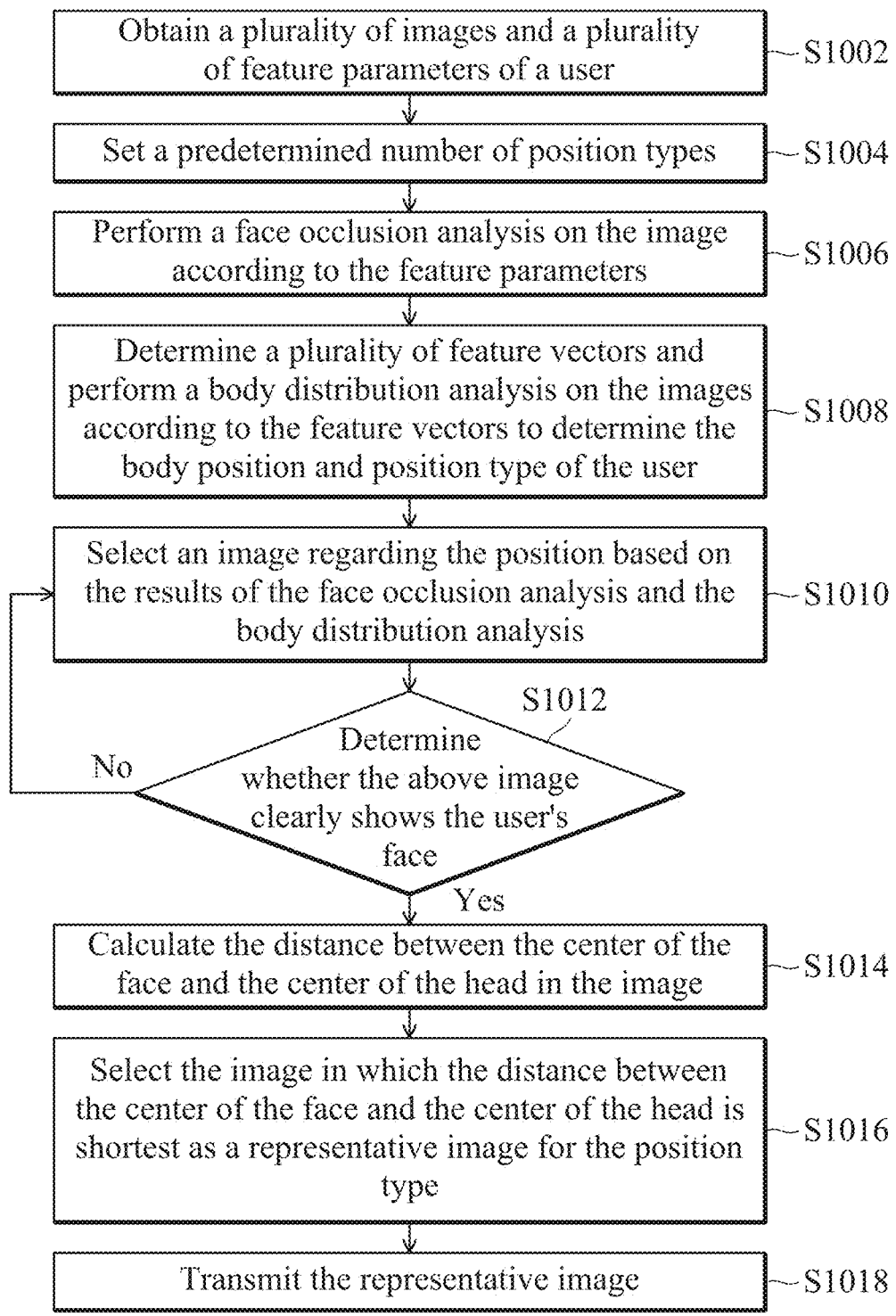
FIG. 10 shows a flow chart of determination of a representative image for a position type by using an image detection method according to an exemplary embodiment of the present invention.

FIG. 10 shows a flow chart of determination of a representative image for a position type by using an image detection method according to an exemplary embodiment of the present invention. In Step S1002, the image detection device 10 obtains a plurality of images and a plurality of feature parameters of a user. In Step S1004, the processor 200 sets a predetermined number of position types. In Step S1006, the processor 200 performs a face occlusion analysis on the image according to the feature parameters.

Then, in Step S1008, the processor 200 determines a plurality of feature vectors and performs a body distribution analysis on the images according to the feature vectors to determine the body position and position type of the user. In Step S1010, the processor 200 selects an image regarding the position based on the results of the face occlusion analysis and the body distribution analysis. In Step S1012, the processor 200 determines whether the above image clearly shows the user's face.

If the image does not clearly shows the user's face, the method returns to Step S1010, and the processor 200 selects another image regarding the type of the position. If the image clearly shows the user's face, method proceeds to Step S1014 in which the processor 200 calculates the distance between the center of the face and the center of the head in the image. Then, in step S1016, the processor 200 selects the image in which the distance between the center of the face and the center of the head is shortest as a representative image for the position type. In Step S1018, the processor 200 transmits the representative image.

The ordinal numbers in the specification and the scope of the patent application, such as "first", "second", "third", etc., have no sequential relationship with each other, and are only used to distinguish between two different components with the same name. The term "coupled" in this specification refers to a variety of direct or indirect electrical connections.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An image detection method for determining a position of a user, comprising:
    obtaining a plurality of images of the user;
    dividing each of the plurality of images of the user into a plurality of region bases;
    determining whether the user moves according to the images;
    obtaining a plurality of feature parameters of the plurality of image;
    performing a body distribution analysis and a face occlusion analysis on the plurality of images according to the feature parameters to calculate detection results of the feature parameters in each region base;
    determining the position of the user according to the detection results;
    calculating pixels contained in each of the plurality of images;
    performing a subtraction operation on two images of the plurality of images to obtain a pixel difference;
    determining whether the pixel difference is greater than a predetermined pixel value;
    in response to the pixel difference being not greater than the predetermined pixel value, determining whether the user's nose is covered; and
    determining a frequency for obtaining the plurality of images of the user according to a result of determining whether the user's nose is covered.

2. The image detection method as claimed in claim 1, further comprising:
    determining whether the user moves according to the pixel difference.

3. The image detection method as claimed in claim 2, wherein the plurality of feature parameters comprise the user's trunk, face, head, eyes, nose, mouth, ears, hands, feet, and a distance between center of the face and center of the head.

4. The image detection method as claimed in claim 3, further comprising:
    in response to the user's nose being covered, determining that the position of the user is a high-risk position;
    in response to the user's nose being not covered, determining that the position of the user is a low-risk position;
    wherein determining the frequency for obtaining the plurality of images of the user according to the result of determining whether the user's nose is covered comprises:
    in response to the position of the user being the low-risk position, obtaining the plurality of images of the user at a first frequency; and
    in response to the position of the user being the high-risk position, obtaining the plurality of images of the user at a second frequency, wherein the second frequency is higher than the first frequency.

5. The image detection method as claimed in claim 4, wherein in response to the pixel difference being greater than the predetermined pixel value or in response to determining that the nose is covered according to the corresponding feature parameters, the position is determined to be the high-risk position.

6. The image detection method as claimed in claim 1, wherein the face occlusion analysis is performed by using the user's eyes, nose, and mouth as the feature parameters, and whether a face occlusion status occurs is determined according to the corresponding detection results.

7. The image detection method as claimed in claim 1, wherein the body distribution analysis is performed to determine whether the user is sleeping in the supine position, on either side, or in the prone position.

8. The image detection method as claimed in claim 7, further comprising:
    in response to determining that the user is sleeping on his side or in the prone position and a determined confidence level being lower than a predetermined confidence level, determining the position of the user according to a result of the face occlusion analysis.

9. The image detection method as claimed in claim 1, further comprising:
    in response to determining that the position of the user is a high-risk position, transmitting a warning message to the user's parents.

10. An image detection device, comprising:
    a sensor capturing a plurality of images of a user;
    a notification device; and
    a processor dividing each of the plurality of images of the user into a plurality of region bases, determining whether the user moves according to the plurality of images, and obtaining a plurality of feature parameters of the plurality of images,
    wherein the processor performs a body distribution analysis and a face occlusion analysis on the images according to the feature parameters to calculate detection results of the feature parameters in each region base and determines a position of the user according to the detection results,
    wherein the processor calculates pixels contained in each of the plurality of images and performs a subtraction operation on two images of the plurality of images to obtain a pixel difference,
    wherein the processor determines whether the pixel difference is greater than a predetermined pixel value and determines whether the user's nose is covered in response to the pixel difference being not greater than the predetermined pixel value, and
    wherein the sensor obtains the plurality of images of the user at a first frequency or a second frequency according to a result of determining whether the user's nose is covered.

11. The image detection device as claimed in claim 10,
    wherein the processor determines whether the user moves according to the pixel difference, and
    wherein the feature parameters comprise the user's trunk, face, head, eyes, nose, mouth, ears, hands, feet, and a distance between center of the face and center of the head.

12. The image detection device as claimed in claim 10,
    wherein the processor determines that the position of the user is a high-risk position in response to the user's nose being covered and determines that the position of the user is a low-risk position in response to the user's nose being not covered,
    wherein in response to the position of the user being the low-risk position, the sensor obtains the plurality of images of the user at the first frequency;

wherein in response to the position of the user being the high-risk position, the sensors obtains the plurality of images of the user at the second frequency, and wherein the second frequency is higher than the first frequency.

\* \* \* \* \*